United States Patent [19]

Takita et al.

[11] 4,238,391

[45] Dec. 9, 1980

[54] 3-[(S)-1'-PHENYLETHYLAMINO]-PROPYLAMINOBLEOMYCIN, NON-TOXIC SALT THEREOF, AND METHOD FOR PRODUCING SAME

[75] Inventors: Tomohisa Takita, Asaka; Akio Fujii, Kamakura; Takeyo Fukuoka, Tokyo; Yasuhiko Muraoka, Kitamoto; Osamu Yoshioka, Yono; Hamao Umezawa, Tokyo, all of Japan

[73] Assignee: Nippon Kayaku Kabushiki Kaisha, Tokyo, Japan

[21] Appl. No.: 58,526

[22] Filed: Jul. 18, 1979

Related U.S. Application Data

[62] Division of Ser. No. 915,805, Jun. 15, 1978.

[30] Foreign Application Priority Data

Jul. 1, 1977 [JP] Japan .................................. 52-77770
Oct. 14, 1977 [JP] Japan .................................. 52-122485

[51] Int. Cl.³ ............................................. C07C 103/52
[52] U.S. Cl. .......................... 260/112.5 R; 536/17 R; 424/177
[58] Field of Search ..................... 536/17; 260/112.5 R

[56] References Cited

U.S. PATENT DOCUMENTS

| | | | |
|---|---|---|---|
| 3,922,262 | 11/1975 | Umezawa et al. | 536/17 |
| 3,971,822 | 7/1976 | Chibata et al. | 260/112.5 R |
| 4,007,219 | 2/1977 | Hassall et al. | 260/112.5 R |
| 4,032,567 | 6/1977 | Klieger et al. | 260/112.5 R |
| 4,128,542 | 12/1978 | Atherton et al. | 260/112.5 R |

FOREIGN PATENT DOCUMENTS

49-61180 6/1974 Japan .
49-70980 7/1974 Japan .

*Primary Examiner*—Delbert R. Phillips
*Assistant Examiner*—Blondel Hazel
*Attorney, Agent, or Firm*—Schuyler, Banner, Birch, McKie & Beckett

[57] ABSTRACT

Novel 3-[(S)-1'-phenylethylamino]propylaminobleomycin obtained by reacting a reactive derivative of the carboxyl group of bleomycinic acid with N-[(S)-1'-phenylethyl]-1,3-diaminopropane, a non-toxic salt of said novel bleomycin, and a method for producing the novel bleomycin. Because of much reduction in the side effect causing pulmonary fibrosis, the novel bleomycin is more useful than a commercial bleomycin complex which gives rise to said undesirable side effect.

5 Claims, 4 Drawing Figures

3-[(S)-1'-PHENYLETHYLAMINO]PROPYLAMINO-BLEOMYCIN, NON-TOXIC SALT THEREOF, AND METHOD FOR PRODUCING SAME

This is a division of application Ser. No. 915,805 filed June 15, 1978.

This invention relates to a novel bleomycin, non-toxic salts thereof, and a method for producing said novel bleomycin. More particularly, it relates to 3-[(S)-1'-phenylethylamino]propylaminobleomycin represented by the formula

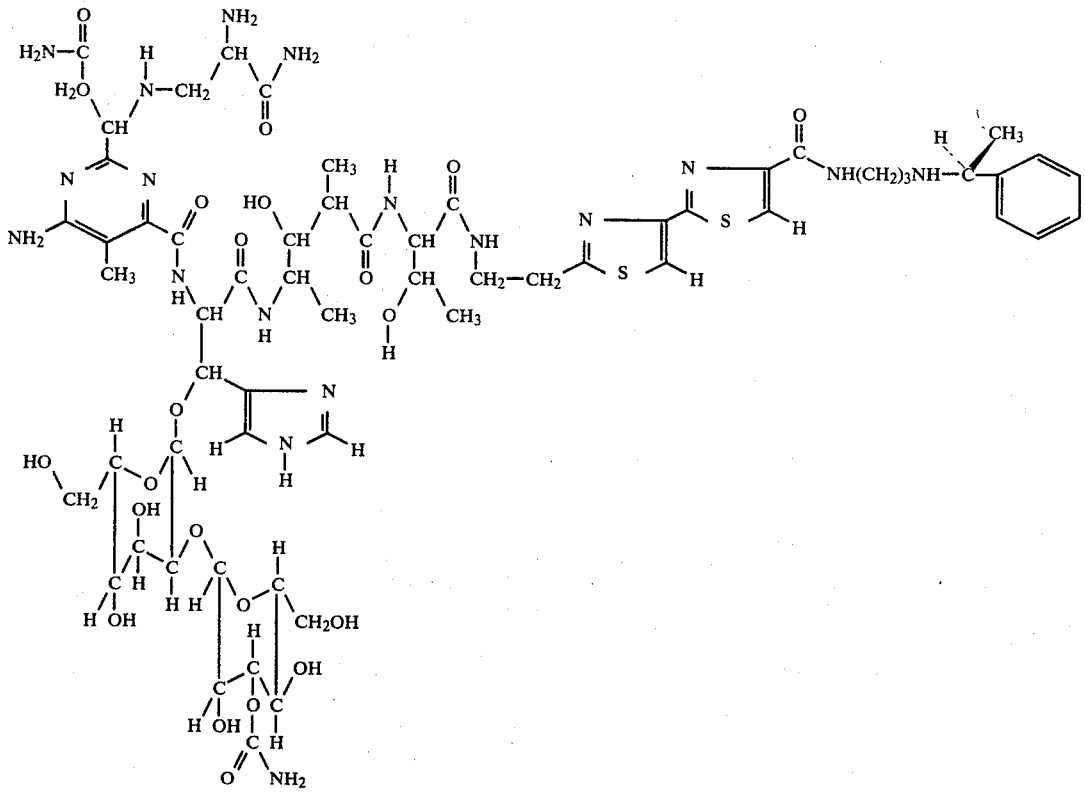

(I), non-toxic salts thereof, and a method for producing said novel bleomycin.

Bleomycins are carcinostatic antibiotic substances discovered by Umezawa, one of the present inventors, and collaborators [Journal of Antibiotics, 19A, 200 (1966)], which are water-soluble basic glycopeptides produced by *Actinomycete Streptomyces verticillus* and are capable of readily chelating one atom of divalent copper. In normal cultivation, 16 components of bleomycins are produced and isolated [for example, Umezawa et al., Journal of Antibiotics, 19A, 210 (1966)]. Of the bleomycins, a mixture of copper-free $A_1$, $A_2$, $A_5$, $B_2$ and demethyl $A_2$ (hereinafter referred to as "Bleomycin complex") has been widely used in clinical fields of cancer therapy and has proved to be successful particularly in the therapy of squamous cell carcinoma as major target, skin cancer, head and neck cancer, cancer of the uterine cervix, lung cancer, and malignant lymphoma.

Regarding the side effect, however, there have been reported cases of pumonary fibrosis and other undesirable occurences. Of the side effects exhibited by bloemycins, the most fearful is pulmonary fibrosis. It is readily imaginable that the carcinostatic activity of bleomycins might be more effectively manifested in clinical fields if the above-noted side effect could be more or less reduced.

Under the circumstances, the present inventors had engaged for years in the synthesis of various bleomycins and in various animal tests on their carcinostatic activity as well as their toxicity including pulmonary fibrosis as major test item. As a result, it was found that 3-[(S)-1'-phenylethylamino]propylaminobleomycin (hereinafter referred to as "NK631" including both copper-containing and copper-free forms), which is a new bleomycin obtained by reacting a reactive derivative of the carboxyl group of bleomycinic acid with N-[S)-1'-phenylethyl]-1,3-diaminopropane, is markedly reduced in the side effect causing pulmonary fibrosis and is not deteriorated in carcinostatic activity, as compared with a commercial bleomycin complex and other known bleomycins. The present invention has been accomplished based on the above finding.

An object of this invention is to provide a novel bleomycin, 3-[(S)-1'-phenylethylamino]propylaminobleomycin, a non-toxic salt thereof, and a method for producing said novel bleomycin.

Other objects and advantages of this invention will become apparent from the following description.

The excellent bioactivity of the present bleomycin represented by the formula (I) is illustrated below with reference to Experimental Examples.

The bioactivity of NK631 was examined with respect to the following 4 test items by comparing with a commercial bleomycin complex and 3-[(R,S)-1'-phenylethylamino]propylaminobleomycin monosulfate (copper-free form) (hereinafter referred to as "RS form"). The RS form was obtained by a fermentation procedure disclosed in U.S. Pat. No. 3,846,400.

1. Pulmonary fibrosis
2. Anti-tumor activity
3. Antimicrobial activity
4. Toxicity

1. Toxicity to the lung of mice (fibrosis)

ICR strain mice (male, 15 weeks old), 12 in number per group, were used. The dosage of each pharmaceutical test preparation was 5 mg/kg. The dose was administered by intraperitoneal injection, once a day, for 10 consecutive days. After administration, the mice were bred for 5 weeks. After observation, the mice were slaughtered and autopsied to determine the extent of pulmonary fibrosis. The incidence and grade of pulmonary fibrosis in mice administered with the novel bleomycin of this invention, a commercial bleomycin complex and RS form were compared. The results obtained were as shown in Table 1.

Table 1

|  | Incidence | | Grade | |
|---|---|---|---|---|
|  | Number of mice with pulmonary fibrosis (%) | Relative value | Total score of pulmonary* fibrosis/total number of samples | Relative value |
| NK631 monosulfate (copper-free form) | 4/12 (0.33) | 0.36 | 6/36 (0.17) | 0.25 |
| RS form | 7/12 (0.58) | 0.63 | 12/36 (0.33) | 0.49 |
| Bleomycin complex | 11/12 (0.92) | 1.0 | 24/36 (0.67) | 1.0 |

Note:
*0 point: No fibrosis
1 point: Accumulation of exudate in aveolus and fibrosis-like change in alveolar septum
2 points: Fibrosis in several areas
4 points: Scattered fibrosis
6 points: Fibrosis in more than two-thirds of the total area As is apparent from the above results, as compared with the cases of RS form and bleomycin complex, the fibrosis due to NK631 monosulfate (copper-free form) was reduced to about ½ and ⅓, respectively, in incidence and about ½ and ¼, respectively, in grade, indicating the usefulness of NK631 monosulfate in clinical fields.

2. Anti-tumor activity 2-1. Action on cultivated HeLa S₃ cell $ID_{50}$ for each bleomycin was calculated from the percentage growth inhibition in 72 hours of culture in the presence of each bleomycin. $ID_{50}$ for NK631 was found to be 0.82 mcg/ml, as contrasted to 1.70 mcg/ml for Bleomycin complex, indicating that NK631 inhibited the cell growth twice as strongly as Bleomycin complex. $ID_{50}$ for RS form was found to be 0.80 mcg/ml, indicating that the inhibiting effect was comparable to that of NK631 monosulfate (copper-free form).

2-2. Carcinostatic activity to mouse Ehrlich cancer (solid tumor)

Each $2 \times 10^6$ cells were transplanted subcutaneously into the inguinal region of ICR strain mice (male, 6 weeks old). After 24 hours, each mouse was administered with test preparations in the same manner as described in 1-2 above. On the 15th day after the subcutaneous transplantation, tumors were removed from each mouse and compared the weight with that of tumors developed in the control group, which had received no treatment, to determine the percentage inhibition.

As shown in Table 2, the carcinostatic activity of NK631 monosulfate (copper-free) was comparable to that of the RS form and about 1.4 times as high as that of the Bleomycin complex.

Table 2

| Dosage mg/kg × 10 | Percentage inhibition | | |
|---|---|---|---|
|  | NK631 monosulfate (Cu-free) | RS-form | Bleomycin complex |
| 2.7 | 84 | 78 | 67 |
| 0.9 | 68 | 60 | 55 |
| 0.3 | 39 | 51 | 49 |
| 0.1 | 24 | 51 | 24 |
| 0.03 | 19 | 13 | 21 |
| 0 | 0 | 0 | 0 |
| $ID_{50}$ mg/kg/day | 0.35 | 0.31 | 0.49 |

2-3. Carcinostatic activity against ascites hepatoma (ascites type) in rats

Each $1 \times 10^6$ AH66 cells were transplanted intraperitoneally into Donryu strain rats. After 24 hours, the test preparation was intraperitoneally administered once a day for 10 consecutive days. During a period of 30 days after the transplantation, the weight of each rat and the number of dead and survival were observed.

Table 3

| Dosage mg/kg × 10 | Relative value of average survival days | | |
|---|---|---|---|
|  | NK631 monosulfate (Cu-free) | RS-form | Bleomycin complex |
| 3.12 | 296 | 298 | 241 |
| 1.56 | 269 | 257 | 257 |
| 0.78 | 216 | 196 | 145 |
| 0.39 | 163 | 149 | 116 |
| 0.19 | 116 | 121 | 110 |
| 0 | 100 | 100 | 100 |

As shown in Table 3, in the activity against AH66 ascites hepatoma, NK631 monosulfate (copper-free form) was comparable to the RS-form and superior to the Bleomycin complex at every dosage.

2-4. Inhibitory activity against mouse squamous cell carcinoma induced by 20-methylcholanthrene (hereinafter referred to as "20-MC")

An acetone solution of 20-MC was topically applied to the sheared back of ddy strain mice (male, 10 weeks old), twice a week, for 18 weeks. After 5 weeks from the beginning of the 20-MC treatment, 62.5 mcg/mouse of the test preparation was intraperitoneally applied, twice a week, during a period of 15 weeks. Within the first week after completion of the administration of test preparation, the region where 20-MC had been applied was pathologically examined for the incidence of carcinogenesis.

As shown in Table 4, NK631 monosulfate (copper-free form) and RS-form were slightly more effective than the bleomycin complex in inhibiting the carcinogenesis due to 20-MC.

Table 4

|  | Mortality | Incidence of carcinogenesis (%) | Percentage inhibition |
|---|---|---|---|
| NK631 monosulfate (copper-free) | 1/12 | 5/11 (45.4) | 47.8 |
| RS-form | 1/12 | 5/11 (45.4) | 47.8 |
| Bleomycin complex | 2/12 | 5/10 (50.0) | 42.5 |
| Control | 1/24 | 20/23 (86.9) | 0 |

As seen from the above results, NK631 monosulfate (copper-free form) clearly showed a superior antitumor activity compared with a commercial Bleomycin complex.

3. Antimicrobial activity

The antimicrobial potency was assayed by the cup method against Mycobacterium 607 and *Bacillus subtilis* PCI by using bleomycin $A_2$ as standard (1,000 U/mg). The results were as shown in Table 5.

Table 5

|  | M. 607 | B. Sub. |
|---|---|---|
| NK631 monosulfate (Cu-free) | 7848 | 1550 |
| RS-form | 7535 | 1400 |
| Bleomycin complex | 1234 | 886 |

As is apparent from Table 5, NK631 monosulfate (copper-free form) and the RS-form showed far superior antimicrobial potencies than that of the Bleomycin complex.

4. Toxicity 4-1. Acute toxicity in intraperitoneal route ($LD_{50}$) in rats As shown in Table 6, $LD_{50}$ value to rat in NK631 monosulfate (copper-free form) which is approximately comparable to those for the Bleomycin complex and RS-form.

Table 6

|  |  | $LD_{50}$ mg(w)/kg | Confidence limits (5% level of significance) |
|---|---|---|---|
| Rat | NK631 monosulfate (Cu-free) | 155.0 | 133.6–179.8 |
|  | RS-form | 150.6 | 129.0–170.6 |
|  | Bleomycin complex | 168.0 | 130.0–217.0 |

4-2. Subacute and chronic toxicity in rats and dogs

NK631 monosulfate (copper-free form) was comparable to Bleomycin complex in the subacute and chronic toxicity in rats and dogs. Further, special mention should be made of the fact that necrosis of injected site was observed in all cases of dogs administered with a high dose of Bleomycin complex (1.2 mg/kg 90 injections), but in none of the cases of dogs administered with identical dose of NK631 monosulfate (copper-free form). Toxicity of NK631 monosulfate (copper-free form) to the lung was also lower than that of the Bleomycin complex.

From the above results, toxicity of NK631 monosulfate (copper-free form) is comparable to that of Bleomycin complex, except for the toxicity to lung and the necrosis.

5. Summary

From the test results described above, it is concluded that NK631 is a novel compound having the characteristics of:

(1) an extremely low toxicity to the lung;
(2) an antimicrobial and antitumor activity superior to that of the commercial bleomycin complex;
(3) a systemic toxicity comparable to that of the commercial bleomycin complex; and
(4) a low local toxicity to the injected site.

Accordingly, NK631 is expected to be useful in clinical fields.

The novel bleomycin of this invention, NK631, is synthesized by reacting a reactive derivative of the carboxyl group of bleomycinic acid represented by the formula

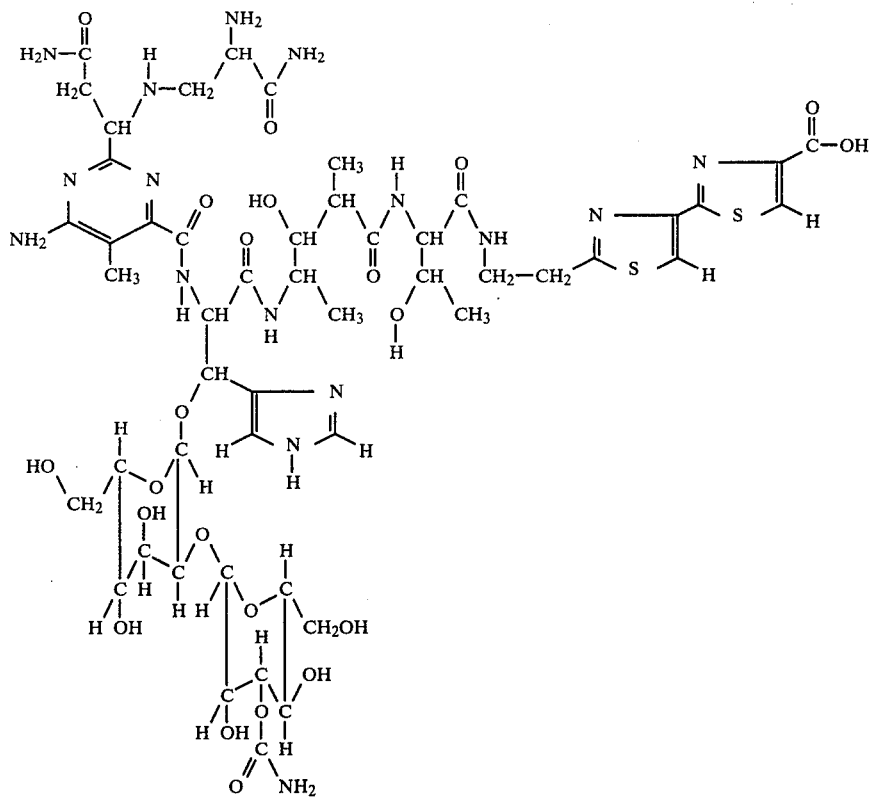

(II)

with N-[(S)-1'-phenylethyl]-1,3-diaminopropane. More particularly, it can be prepared by (1) reacting bleomycinic acid with N-[(S)-1'-phenylethylamino]-1,3-diaminopropane in the presence of an activating reagent, or (2) reacting bleomycinic acid 3-aminopropyl ester or its N-monosubstituted derivative with N-[(S)-1'-phenylethyl]-1,3-diaminopropane. Detailed description of these procedures is given below.

The bleomycinic acid used in the procedure (1) is a known compound obtained by enzymatic cleavage of bleomycin $B_2$ according to the method disclosed in U.S. Pat. Nos. 3,843,448 and 3,846,400.

Another starting material, i.e. N-[(S)-1'-phenylethyl]-1,3-diaminopropane, is a novel compound first synthesized by the present inventors in the following manner.

Phenylethylamine cooled at about 0° C. is admixed with an approximately equivalent amount of acrylonitrile. The mixture is kept at 80° to 100° C. for 10 to 24 hours to complete the reaction. The excess acrylonitrile is then removed by distillation under reduced pressure and the residue is further distilled to obtain 3-[(S)-1'-phenylethylamino]propionitrile. The compound thus obtained is reduced in a customary manner, for example, in the presence of Raney nickel to yield the intended N-[(S)-1'-phenylethyl-1,3-diaminopropane] (hereinafter referred to as "amino compound"). Physico-chemical properties of this compound are as listed in Table 7.

Table 7

| | | Free base | Dihydrochloride |
|---|---|---|---|
| (1) | Appearance | colorless liquid at room temp. | white needle crystal |
| (2) | Melting point | — | 223.5°–224° C. |
| (3) | Boiling point | 95°–103° C. (2 mmHg) | — |
| (4) | Ultraviolet absorption maxima (mμ) | 241, 247, 252, 257, 263, 267 (methanol) | 250, 256, 259, 266 (distilled water) |
| (5) | Molecular extinction coefficient, ε (256 mμ) | — | 206 (distil. water) |
| (6) | Specific rotation $(\alpha)_D^{25}$ | — | −20.6° (c = 1, distil. water) |
| | $D_D^{26}$ | −56.38° (undiluted, l = 1) | — |
| (7) | Rf value in TL-chromatography, n-propanol-pyridine-acetic acid-water (15:10:3:12 V/V), Avicel-SF ® | 0.73 | 0.73 |
| (8) | Rm value in high voltage electropheresis, formic acid-acetic acid-water (25:75:900 V/V), | 1.52 | 1.52 |

Table 7-continued

| | | Free base | Dihydrochloride |
|---|---|---|---|
| | Avicel-SF ®, 800 V, 10 min., Rm of alanine = 1.0 | | |
| (9) | IR absorption spectrum, cm$^{-1}$, KBr | 700, 760, 820, 910, 1,025, 1,080 1,130, 1,200, 1,305, 1,350, 1,370, 1,450, 1,495, 1,605, 2,850, 2,940, 3,300, 3,375 | 690, 750, 820, 910, 980, 1,020, 1,065, 1,075, 1,150, 1,205, 1,385, 1,460, 1,500, 1,515, 1,590, 2,500, 2,850, 3,000, 3,500 |
| (10) | Molecular formula (molecular weight) | $C_{11}H_{18}N_2$ (178.28) | $C_{11}H_{20}N_2Cl_2$ (251.20) |

Examples of the useful activating reagents include 6-chloro-1-p-chlorobenzenesulfonyloxybenzotriazole (CCBT), N-ethyl-5-phenylisoxazolium-3'-sulfonate (NEPIS), N-tert-butyl-5-methylisoxazolium perchlorate, N-ethoxycarbonyl-2-ethoxy-1,2-dihydroquinoline, di-p-nitrophenyl sulfite, tri-p-nitrophenyl phosphite, p-nitrophenyl trichloroacetate, N-hydroxysuccinimide, dicyclohexylcarbodiimide (DCC), 1-ethyl-3-(3-dimethylaminopropyl)-carbodiimide, 1-cyclohexyl-3-(2-morpholinoethyl)carbodiimide, diphenylcarbodiimide, di-p-toluylcarbodiimide, diisopropylcarbodiimide, p-nitrophenol, pentachlorophenol, and benzyl alcohol.

Detailed description of the procedure (1):

Figure 1:
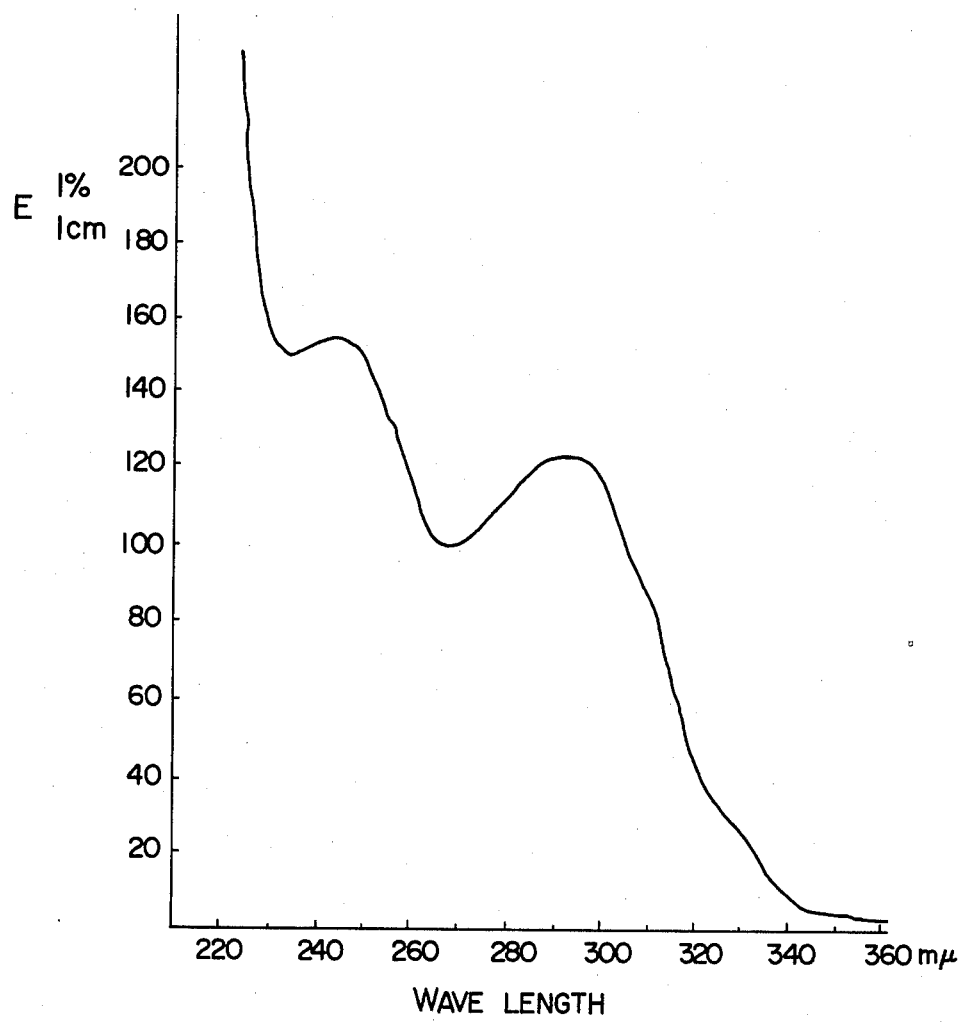

Bleomycinic acid (copper-containing form) is dissolved in water, dimethylformamide, dimethyl sulfoxide, or a mixture thereof. To the solution, while being stirred at 0° to 30° C., is added one of the activating reagents listed above. The resulting solution is adjusted to pH 3–10, suitable for activation, by the addition of an inorganic acid or base such as hydrochloric acid or sodium hydroxide or the addition of an organic acid or base such as trichloroacetic acid or N-methylmorpholine. Upon such a treatment, activation of the carboxyl group of bleomycinic acid is initiated. Immediately or within 30 minutes after the treatment, the reactant solution is admixed with the amino compound (hereinbefore defined) as such or after having been adjusted to pH about 7.0. The mixture is then kept at 0° to 30° C. for 1 to 24 hours to allow the reaction to proceed, thereby yielding NK631. A suitable proportion of the activating reagent or the amino compound is 1 to 10 equivalents for 1 equivalent of bleomycinic acid.

In order to isolate NK631 from the reaction mixture, at first the bleomycin compounds are exhaustively precipitated by the addition of 5 to 10 volumes of acetone for 1 volume of the reaction mixture. The precipitate is collected by filtration, washed with acetone, and dissolved in a least possible quantity of distilled water. The resulting aqueous solution is immediately adjusted to pH 6.0 with hydrochloric acid or the like and applied on the top of a chromatographic column containing CM-Sephadex ® C-25 (NH$_4^+$ type, supplied by Pharmacia Fine Chemicals.) packed in an aqueous ammonium chloride solution. The unreacted bleomycinic acid passes through the column without being adsorbed. The NK631 adsorbed on the resin is eluted with aqueous ammonia chloride solutions of gradient concentrations, increasing stepwise or continuously from 0.05 M to 1.0 M. NK631 is contained in blue effluent fractions, at about 0.35 M to 0.45 M of ammonium chloride concentration, which show ultraviolet absorption at 292 m$\mu$. These fractions are separately collected and passed through Amberite ® XAD-2 (Rohm and Haas Co.) or Diaion ® HP40 (Mitsubishi Chemical Co.). The adsorbed NK631 is washed with water and eluted to give a desalted effluent, from which a pure, blue, amorphous powder of NK631 (copper-containing form) is obtained. Hydrochloride and sulfate of NK631 are obtained by eluting with aqueous methanol containing hydrochloric acid and sulfuric acid, respectively. In this process, unreacted bleomycinic acid can be conveniently recovered. The procedural step described above, wherein CM-Sephadex ® C-25 (a tradename for an cation-exchange Sephadex composed of microscopic beads of carboxymethyl groups derivative from polysaccharide dextran, manufactured and sold by Pharmacia Fine Chemicals Inc., Sweden) is employed, is an illustrative example and can be modified to some degree without substantially affecting the results. For instance, aqueous chloride or aqueous ammonium sulfate can be used as eluent.

The removal of copper from the copper-containing NK631 obtained above can be effected by applying any of the known methods in which copper is removed by reacting with hydrogen sulfide to convert the copper into cupric sulfide which is precipitated; by reducing the copper to zero-valent copper with a reducing agent (U.S. Pat. No. 3,646,197); by extracting copper with an organic solvent containing a chelating agent such as dithizone [Umezawa et al., Journal of Antibiotics, 19A, 210 (1960)]; or by the use of a non-ionic-exchange macroreticular resin (U.S. Pat. No. 3,929,993). An example of the copper-removing procedure is described below.

NK631 (copper-containing form) is dissolved in distilled water and the solution is poured into a resin column containing Amberlite ® XAD-2 (a tradename for an absorbent resin composed of a styrene-divinylbenzene co-polymer manufactured and sold by Rohome & Haas Co., U.S.A.) or Diaion ® HP40 (a tradename for an absorbent resin composed of a styrene-divinylbenzene co-polymer manufactured and sold by Mitsubishi Chemical Co., Japan) packed in distilled water to allow the NK631 to be adsorbed. The column is then washed with a 5% aqueous solution of ethylenediaminetetraacetic acid disodium (hereinafter referred to as "EDTA.-Na$_2$"), whereby the copper ion is carried away by the EDTA.Na$_2$ solution, leaving behind copper-free NK631 on the resin. The resin is washed with an aqueous solution of a salt such as sodium chloride, sodium sulfate or sodium acetate to remove EDTA.Na$_2$, and then with distilled water. Finally, an acidified methanol-water mixture such as, for example, a mixture of methanol and 0.0025 N hydrochloric acid (1:1 V/V) is passed through the column to elute a substance showing an ultraviolet absorption at 290 m$\mu$. This fraction is collected, concentrated, adjusted to pH 6.0, and freeze-dried to yield a pale-yellowish white amorphous powder of NK631 dihyrochloride (copper-free form).

As an acid to be used to prepare an acidified methanol-water mixture, any acids can be used so long as they are pharmaceutically acceptable. For example, when sulfuric acid or acetic acid is used, a powder of NK631 monosulfate or diacetic acid salt (copper-free form) is obtained.

The KN631 of this invention can be converted in a customary way into other non-toxic salts such as, for example, sulfate and acetic salt which can be also obtained by changing arbitrarily the acid employed in eluting.

In the procedure (1), since the amino compound reacts with the activated carboxyl group of bleomycinic acid owing to the presence of an activating reagent employed in the polypeptide synthesis, the condensation reaction proceeds smoothly under extremely mild conditions. Consequently, only the primary amino group of the amino compound reacts with the activated carboxyl group while the secondary imino group does not participate in the reaction, thus yielding preferentially NK631. This is a remarkable advantage of the procedure (1).

Detailed description of the procedure (2):

The 3-aminopropyl ester of bleomycinic acid employed in the procedure (2) is easily obtained in the form of dihydrochloride (copper-containing form) by thermally decomposing bleomycin $A_2$ to form 3-(methylmercapto)propylaminobleomycin and reacting the resultant bleomycin with a halogenonitrile, halogenoacetic acid, halogenoacetate ester, or halogenoacetamide in an acidic solution (U.S. Pat. No. 3,886,133).

The N-monosubstituted derivative of 3-aminopropyl ester of bleomycinic acid, which has its amino group protected, is obtained in a high yield by dissolving dihydrochloride of 3-aminopropyl ester of bleomycinic acid in water or an organic solvent such as methanol or a mixture thereof, then adding slowly to the resulting solution, while stirring vigorously, an equivalent amount or a slight excess of one of the known amino group-protecting reagents, in the form of powder or solution in an organic solvent such as methanol, and allowing the reaction to proceed at room temperature or ice-cooled temperature while continually keeping pH of the reactant mixture at 5.0 to 7.5 by adding an organic base such as, for example, trimethylamine, triethylamine, pyridine, 1,3-diazabicyclo-[5,4,0]-7-undecene, 1,5-diazabicyclo-[3,4,0]-5-nonene, 1,4-diazabicyclo[2,2,2]-octane, or N-methylmorpholine. Typical of such N-monosubstituted derivatives are monohydrochloride of 3-acetylaminopropyl ester of bleomycinic acid, 3-succinylaminopropyl ester of bleomycinic acid, monohydrochloride of 3-benzoylaminopropyl ester of bleomycinic acid, monohydrochloride of 3-benzyloxycarbonylaminopropyl ester of bleomycinic acid, monohydrochloride of 3-p-toluenesulfonylaminopropyl ester of bleomycinic acid, monohydrochloride of 3-(2,4-dinitrophenyl)aminopropyl ester of bleomycinic acid, monohydrochloride of 3-(3,5-dimethyl-3-oxocyclohexen-1-yl)aminopropyl ester of bleomycinic acid, monohydrochloride of 3-N-tert-butoxycarbonylpropyl ester of bleomycinic acid, and monohydrochloride of 3-N-salicylideneiminopropyl ester of bleomycinic acid (U.S. Pat. No. 3,886,133).

In the procedure (2), NK631 is formed by the reaction between 3-aminopropyl ester or N-monosubstituted 3-aminopropyl ester of bleomycinic acid and the amino compound. In the case of N-monosubstituted 3-aminopropyl ester of bleomycinic acid as starting material, either a pure material or a reaction mixture, which may be concentrated, obtained from 3-aminopropyl ester of bleomycinic acid and an amino group-protecting reagent can be used.

Preferable solvents used in the reaction of 3-aminopropyl ester or N-monosubstituted 3-aminopropyl ester of bleomycinic acid and the amino compound are water and organic solvents such as methanol, dimethylformamide and dimethyl sulfoxide. The reactant mixture is left standing at 0° to 80° C. for 1 to 72 hours under a neutral or alkaline condition to allow the aminolysis reaction to proceed, whereby NK631 is formed. Under the condition of a higher pH, a prolonged reaction time at comparatively low temperatures is desirable, while under the condition of a lower pH, a short reaction time at higher temperatures is preferred. The suitable proportion of the amino compound in the reactant mixture is 1 to 10 equivalents for 1 equivalent of the 3-aminopropyl ester of bleomycinic acid or a N-monosubstituted derivative thereof.

To isolate NK631 from the reaction mixture, at first the bleomycin components are exhaustively precipitated by the addition of 2 to 5 times the volume of reaction mixture of acetone. The precipitate is collected by filtration, washed thoroughly with acetone and then dissolved in the least possible amount of distilled water. The resulting aqueous solution is quickly adjusted to pH 6.0 by adding hydrochloric acid or the like and poured into a chromatographic column of CM-Sephadex ® C-25 ($NH_4^+$ type, supplied by Pharmacia Fine Chemicals) packed in a 0.05 M aqueous ammonium chloride solution to allow the bleomycin components to be adsorbed on the resin. Upon passing through the column aqueous ammonium chloride solution in which the concentration is increased stepwise or continually from 0.05 M to 1.0 M, the unreacted 3-aminopropyl ester of bleomycinic acid or a N-monosubstituted derivative thereof and NK631 are eluted, forming blue bands (UV absorption at 292 mμ) in the effluent stream at ammonium chloride concentrations of 0.15–0.20 M and 0.35–0.45 M, respectively. These fractions are separately collected and desalted by adsorbing on Amberlite ® XAD-2 or Diaion ® HP40, washing with water, and eluting to obtain a blue amorphous powder of NK631 (copper-containing form). Hydrochloride and sulfate are obtained by using methanol-water mixtures acidified with hydrochloric acid and sulfuric acid, respectively, as eluents. The unreacted 3-aminopropyl ester of bleomycinic acid or a N-monosubstituted derivative thereof may be conveniently recovered. The procedural step described above, wherein CM-Sephadex ® C-25 is employed, is an typical illustrative example and can be modified to some degree without substantially affecting the results. For instance, aqueous sodium chloride or aqueous ammonium sulfate can be used as the eluent.

The NK631 thus obtained by the procedure (2) can be converted to the copper-free form by the application of known copper-removing methods described above in connection with the procedure (1). If necessary, it is possible to convert it into other non-toxic salts such as, for example, hydrochloride, sulfate and acetic acid salt.

Principal physicochemical properties of NK631 are as shown in Tables 8 and 9.

The structural formula (I) of NK631 was confirmed in the following way: NK631 monosulfate (copper-free form) was dissolved in heavy water and measured for $^{13}C$-NMR by the proton noise decoupling method using dioxane as internal standard. Signals due to a total of eleven $^{13}C$ atoms contained in the amino compound with side chain and 3-[(S)-1'-phenylethylamino]-propylamino moiety were recognized at 19.4, 26.3, 37.0, 43.5, 58.9, 128.3 (two signals), 130.0 (two signals) and 136.3 ppm. Signals due to other carbon atoms were all corresponded to the signals common to the bleomycin family [Naganawa et al., Journal of Antibiotics, 30, 388 (1977)].

thylamino]propylaminobleomycin (copper-free form) measured in the form of potassium bromide tablet.

The invention is illustrated below in detail with reference to Examples, but the invention is not limited to the Examples.

EXAMPLE 1

Synthesis of dihydrochloride (copper-containing form) and monosulfate (copper-free form) of NK631

Table 8

| | Physicochemical properties of NK631 (copper-containing form) | |
|---|---|---|
| | Dihydrochloride | Monosulfate |
| (1) Appearance | Blue amorphous powder | Blue amorphous powder |
| (2) Solubility | Soluble in water, methanol, dimethyl sulfoxide, dimethylformamide; sparingly soluble in dioxane; insoluble in ethanol, acetone, ether, benzene. | The same as dihydrochloride |
| (3) Melting point (decomp.), °C. | 205–207 | 205–207 |
| (4) Specific rotation (distilled water, C = 1.0) $(\alpha)_{436}^{25}$ | −95.6° | −93.7° |
| (5) TL-chromatography,[1] $R_f$ value | (a) 0.72 (b) 0.75 | (a) 0.72 (b) 0.75 |
| (6) Electrophoresis,[2] Rm value (alanine = 1) | 0.80 | 0.80 |

Note:
[1] (a) Silica Gel G ® (a tradename for an adsorbent for thin layer chromatography composed of silica gel manufactured by Merck Inc., U.S.A.); methanol/10% ammonium acetate/10% ammonia (10:9:1 V/V)
(b) Avicel SF ® (a tradename for an adsorbent for thin-layer chromatography composed of crystalline cellulose manufactured by FMC corporation, U.S.A.); n-propanol/pyridine/acetic acid/water (15:10:3:12)
[2] Avicel SF ®; formic acid/acetic acid/water (25:75:900 V/V); 800 V; 15 minutes Table 9

| | Physicochemical properties of NK631 (copper-free form) | | |
|---|---|---|---|
| | Dihydrochloride | Monosulfate | Di(acetic acid) salt |
| (1) Appearance | Pale yellowish white amorphous powder | Pale yellowish white amorphous powder | Pale yellowish white amorphous powder |
| (2) Solubility | Soluble in water, methanol, acetic acid, DMSO, DMF; sparingly soluble in dioxane; insoluble in ethanol, acetone, ether, benzene | | |
| (3) Melting point (decomp.), °C. | 195–197 | 196–198 | 188–190 |
| (4) Specific rotation (distil. water, c = 1.0) $(\alpha)_{436}^{25}$ | −2.1° | −2.0° | −2.0° |
| (5) TL-chromatography,[1] $R_f$ value | (a) 0.56 (b) 0.70 | (a) 0.56 (b) 0.70 | (a) 0.56 (b) 0.70 |
| (6) Electrophoresis,[2] $R_m$ value (alanine = 1.0) | 0.94 | 0.94 | 0.94 |

Figure 2:
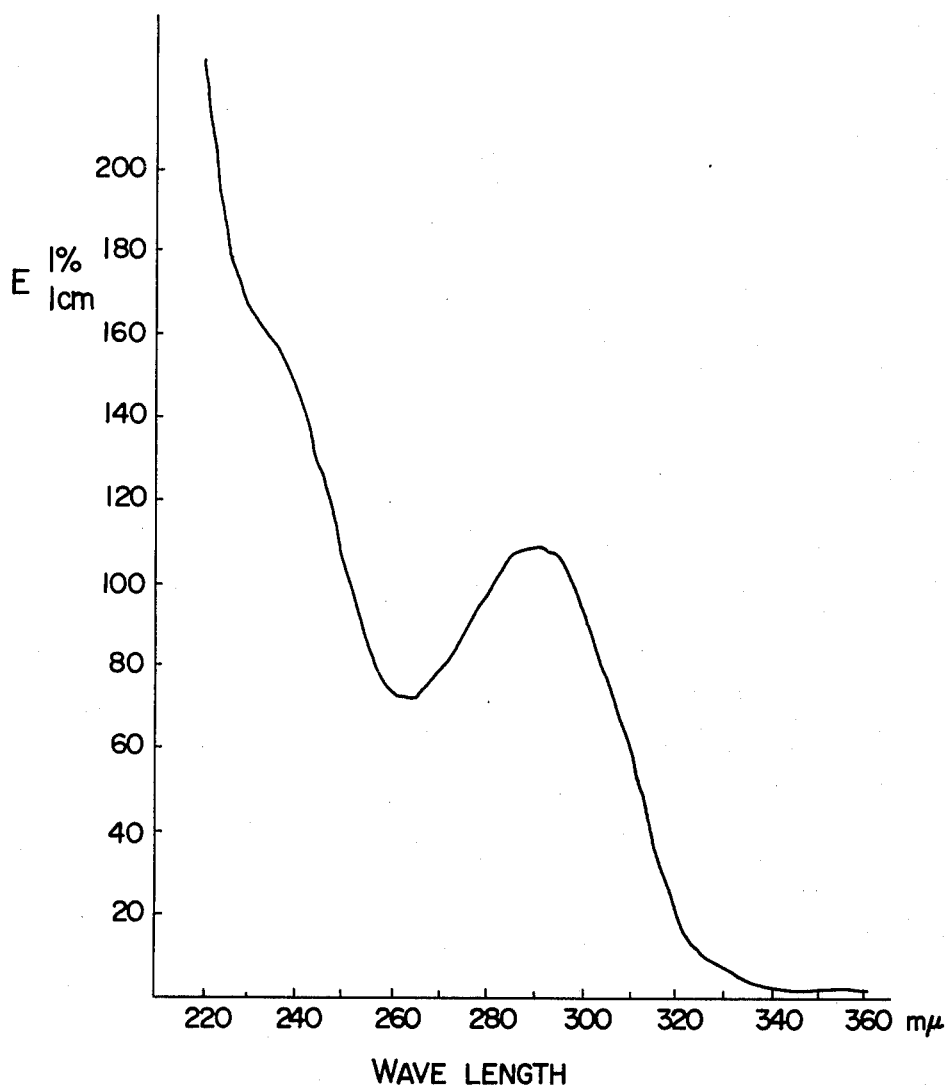
Figure 3:
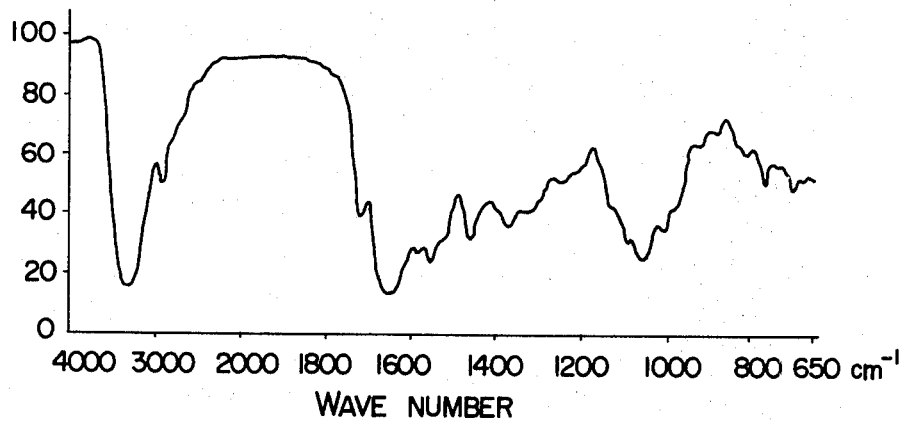
Figure 4:
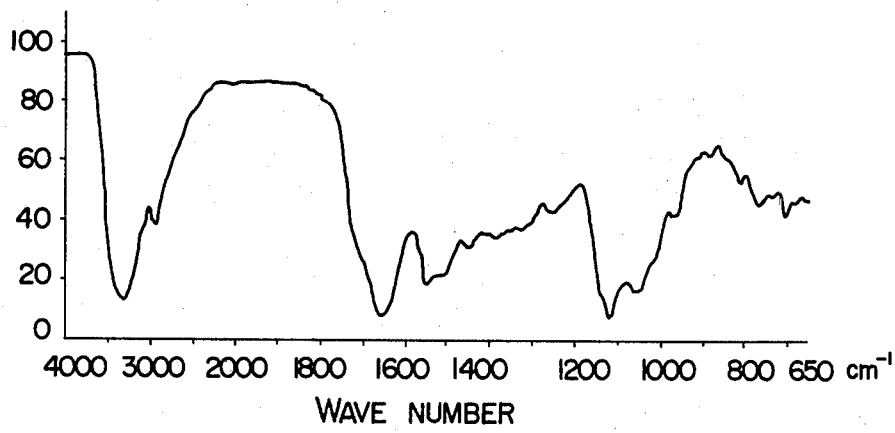

Note:
[1] (a) Silica Gel G ®; methanol/10% ammonium acetate/10% ammonia (10:9:1 V/V) (b) Avicel SF ®; n-propanol/pyridine/acetic acid/water (15:10:3:12)
[2] Avicel SF ®; formic acid/acetic acid/water (25:75:900 V/V); 800 V; 15 minutes In the accompanying drawings, FIGS. 1 and 2 show ultraviolet absorption curves of the bleomycin NK631 of this invention and FIGS. 3 and 4 show infrared absorption curves of NK631.

That is, FIG. 1 shows ultraviolet absorption curve of 3-[(S)-1'-phenylethylamino]propylaminobleomycin dihydrochloride (copper-containing form), FIG. 2 shows ultraviolet absorption curve of 3[(S)-1'-phenylethylamino]-propylaminobleomycin monsulfate (copper-free form), FIG. 3 shows infrared absorption curve of 3-[(S)-1'-phenylethylamino]propylaminobleomycin dihydrochloride (copper-containing form) measured in the form of potassium bromide tablet, and FIG. 4 shows infrared absorption curve of 3-[(S)-1'-phenyle- Step A: In 400 ml of dimethylformamide, was dissolved 15.0 g of bleomycinic acid (copper-containing form). To the solution, while being kept at 0° C. by cooling, were added 1.1 ml of N-methylmorpholine and 10.3 g of CCBT. The mixture was stirred for 5 minutes at 0° C., then admixed with 5.3 g of the amino compound and further stirred for 1 hour. After termination of the reaction by adding 200 ml of a 25% aqueous acetic acid solution, the reaction mixture was mixed with 5 liters of cold acetone to precipitate the reaction product. The precipitate was collected by filtration, washed with acetone, and dissolved in 500 ml of distilled water. The resulting aqueous solution was immediately adjusted to pH 6.0 and poured into a column containing 2 liters of CM-Sephadex ® C-25 ($NH_4^+$ type) packed in 0.05 M aqueous ammonium chloride solution to adsorb bleomycins.

Using aqueous ammonium chloride solution, elution was performed by passing through the column 20 liters of eluent in which the concentration of ammonium chloride was continually increased from 0.05 to 1.0 M. The unreacted bleomycinic acid was found in the effluent at the ammonium chloride concentration of about 0.05 M and NK631 at the ammonium chloride concentration of about 0.45 M. Both fractions, which showed UV absorption at 292 mµ, were separately collected. The NK631-containing fraction was poured into a resin column containing 2.6 liters of Amberlite ® XAD-2. The column was then washed thoroughly with water and eluted with 0.01 N hydrochloric acid in methanol-water (4:1 V/V). A total of 2.5 liters of the blue fraction, which showed UV absorption at 292 mµ, was collected. After evaporating off the methanol from the eluent fraction, the concentrate was adjusted to pH 6.0 with Dowex ® 44 ($OH^-$ type), (a tradename for an anion-exchange resin composed of a co-polymer of epichlorohydrin and ammonia manufactured and sold by Dow Chemical Co., U.S.A.), and was freeze-dried to obtain 16.1 g (9% yield) of NK631 dihydrochloride (copper-containing form) in the form of blue amorphous powder.

By similar treatment, 280 mg of the unreacted bleomycinic acid (copper-containing form) were recovered.

The ultraviolet absorption maxima and antimicrobial potency of the NK631 dihydrochloride (copper-containing form) were as shown below.

UV absorption maxima:
mµ: ($E_{1\,cm}^{1\%}$, distilled water)
242: (151)
292: (121)
Antimicrobial potency: 8,100 u/mg
[Note: The antimicrobial potency was assayed using *Mycobacterium smegmatis* ATCC 607 as assay organism and assuming the potency of bleomycin $A_2$ (copper-free form) as 1,000 u/mg. The same applies hereinafter.]

Step B: In 200 ml of distilled water, was dissolved 10.0 g of the NK631 dihydrochloride (copper-containing form). The solution was poured into a column containing 600 ml of Amberlite ® XAD-2 packed in distilled water. The column was then washed successively with 2 liters of an aqueous solution containing 5% of $EDTA.Na_2$, 2.5 liters of a 5% aqueous sodium sulfate solution, and 630 ml of distilled water. The column was then eluted with 0.0025 N sulfuric acid in methanol-water mixture (1:1 V/V). A total of 900 ml of fractions containing a substance which showed UV absorption at 290 mµ was collected. After removal of methanol by distillation, the residual liquid was adjusted to pH 6.0 with Dowex ® 44 ($OH^-$ type) and freeze-dried to obtain 9.3 g (95% yield) of NK631 monosulfate (copper-free form) in the form of pale yellowish white amorphous powder. This product showed an UV absorption maximum and an antimicrobial potency as shown below.

UV absorption maximum:
mµ: ($E_{1\,cm}^{1\%}$ 0.1 N HCl)
290: (106)
Antimicrobial potency: 7,865 u/mg

EXAMPLE 2

Synthesis of NK631 dihydrochloride (copper-containing form)

In 40 ml of distilled water, was dissolved 1.5 g of bleomycinic acid (copper-containing form). To the stirred solution at 26° C., was added 800 mg of NEPIS while maintaining pH of the reactant mixture at 4.8 to 5.5 by the addition of 0.1 N aqueous sodium hydroxide solution. After 30 minutes, to the mixture was added a solution prepared by dissolving 1.8 g of the amino compound in 20 ml of distilled water and adjusting to pH 7.0 with hydrochloric acid. The mixture was left standing for 20 hours at 26° C. To the reaction mixture was added with stirring 600 ml of cold acetone to precipitate the bleomycin components. The precipitate was collected by filtration, washed with acetone, then dissolved in 30 ml of distilled water and immediately adjusted to pH 6.0 with 0.1 N hydrochloric acid. The resulting aqueous solution was purified by following the procedure described in step A of Example 1 to obtain 932 mg (53% yield) of NK631 dihydrochloride (copper-containing form) in the form of blue amorphous powder having an amtimicrobial potency of 8,073 u/mg.

EXAMPLE 3

Synthesis of NK631 dihydrochloride (copper-containing form)

In 40 ml of dimethyl sulfoxide, was dissolved 1.5 g of bleomycinic acid (copper-containing form). To the stirred solution at 30° C., were added 740 mg of N-ethoxycarbonyl-2-ethoxy-1,2-dihydroquinoline and 0.1 ml of N-methylmorpholine. To the mixture, which had been stirred for 30 minutes, was added with stirring 530 mg of the amino compound and the mixture was left standing for 3 hours at 30° C. To the reaction mixture was added with stirring 600 ml of cold acetone to precipitate bleomycin components. The precipitate was collected by filtration, washed with acetone, then dissolved in 30 ml of distilled water and immediately adjusted to pH 6.0 with 0.1 N hydrochloric acid. The resulting aqueous solution was treated in a manner similar to that in step A of Example 1 to obtain 809 mg (46% yield) of NK631 dihydrochloride (copper-containing form) in the form of blue amorphous powder which showed an antimicrobial potency of 8,028 u/mg.

EXAMPLE 4

Synthesis of NK631 dihydrochloride (copper-containing form)

In 40 ml of distilled water, was dissolved 1.5 g of bleomycinic acid (copper-containing form). After addition of 1.2 g of 1-ethyl-3-(3-dimethylaminopropyl)-carbodiimide hydrochloride at 27° C., the mixture was adjusted to pH 4.5 with 0.1 N hydrochloric acid. After addition of 530 mg of the amino compound, the mixture was again adjusted to pH 5.0 with 1 N hydrochloric acid and left standing for 20 hours at 27° C. To the reaction mixture, was added with stirring 400 ml of cold acetone to precipitate the bleomycin components. The precipitate was collected by filtration, washed with acetone, then dissolved in 30 ml of distilled water and immediately adjusted to pH 6.0 with 0.1 N sodium hydroxide. The resulting aqueous solution was purified by following the procedure described in step A of Example 1 to obtain 440 mg (25% yield) of NK631 dihydrochloride (copper-containing form) in the form of blue amorphous powder having an antimicrobial potency of 7,985 u/mg.

EXAMPLE 5

Synthesis of NK631 dihydrochloride (copper-containing form)

In 16 ml of methanol, was dissolved 9.0 g of bleomycinic acid 3-N-benzoylaminopropyl ester monohydrochloride (copper-containing form). While cooling at 0° C., to the solution was added 9.16 g of the amino compound. After continued stirring for 40 hours at 0° C., cold acetone was added to the reaction mixture to precipitate the reaction products. The precipitate was collected by filtration, washed with acetone, and dissolved in 300 ml of distilled water. The solution was immediately adjusted to pH 6.0 with 0.1 N hydrochloric acid and poured into a column containing 1 liter of CM-Sephadex ® C-25 ($NH_4^+$ type) packed in 0.05 M aqueous ammonium chloride solution to allow the bleomycins to be adsorbed. Using aqueous ammonium chloride solution as eluent, elution was performed by passing through the column 10 liters of eluent in which the concentration of ammonium chloride was continuously increased from 0.05 to 1.0 M. The unreacted 3-N-benzoylaminopropyl ester of bleomycinic acid was found in the effluent at the ammonium chloride concentration of about 0.2 M and NK631 at the ammonium chloride concentration of about 0.45 M. Both fractions, which showed UV absorption at 272 mµ, were separately collected. The NK631-containing fraction was poured into a resin column containing 1.3 liters of Amberlite ® XAD-2. The column was then washed thoroughly with water and eluted with 0.01 N hydrochloric acid in methanol-water mixture (4:1 V/V). A total of 2.5 liters of the blue fraction, which showed UV absorption at 292 mµ, was collected. After having been freed from methanol by distillation and adjusted to pH 6.0 with Dowex ® 44 ($OH^-$ type), the fraction was freeze-dried to obtain 8.2 g (90% yield) of NK631 dihydrochloride (copper-containing form) in the form of blue amorphous powder having an antimicrobial potency of 8,030 u/mg.

By similar treatment, 910 mg of the unreacted bleomycinic acid 3-N-benzoylaminopropyl ester monohydrochloride (copper-containing form) were recovered.

EXAMPLE 6

Synthesis of NK631 dihydrochloride (copper-containing form)

In 3 ml of methanol, was dissolved 950 mg of bleomycinic acid 3-N-p-toluenesulfonylaminopropyl ester monohydrochloride (copper-containing form). To the solution, while being stirred at 0° C., was added 980 mg of the amino compound and the mixture was stirred for 48 hours at 0° C. To the reaction mixture, was added with stirring 15 ml of cold acetone to precipitate bleomycin components. The precipitate was collected by filtration, washed with acetone, then dissolved in 30 ml of distilled water, and immediately adjusted to pH 6.0 with 0.1 N hydrochloric acid. The resulting solution was purified following the procedure described in step A of Example 5 to obtain 833 mg (85% yield) of NK631 dihydrochloride (copper-containing form) in the form of blue amorphous powder having an antimicrobial potency of 8,010 u/mg.

EXAMPLE 7

Synthesis of NK631 dihydrochloride (copper-containing form)

In 5 ml of dimethylformamide, was dissolved 850 mg of bleomycinic acid 3-acetylaminopropyl ester monohydrochloride (copper-containing form). To the solution, while being stirred at 0° C., was added 950 mg of the amino compound and the mixture was stirred for 45 hours at 0° C. To the reaction mixture, was added with stirring 20 ml of cold acetone to precipitate bleomycin components. The precipitate was collected by filtration, washed with acetone, then dissolved in 30 ml of distilled water, and immediately adjusted to pH 6.0 with 0.1 N hydrochloric acid. The resulting solution was treated in the same manner as in step A of Example 5 to obtain 570 mg (63% yield) of NK631 dihydrochloride (copper-containing form) in the form of blue amorphous powder having an antimicrobial potency of 8,010 u/mg.

EXAMPLE 8

Synthesis of NK631 dihydrochloride (copper-containing form)

In 3 ml of dimethyl sulfoxide, was dissolved 900 mg of bleomycinic acid 3-N-(2,4-dinitrophenyl)-aminopropyl ester monohydrochloride (copper-containing form). To the solution, while being stirred at 0° C., was added 793 mg of the amino compound and the mixture was stirred for 24 hours at 0° C. To the reaction mixture, was added with stirring 15 ml of cold acetone to precipitate bleomycin components. The precipitate was collected by filtration, washed with acetone, then dissolved in 30 ml of distilled water, and immediately adjusted to pH 6.0 with 0.1 N hydrochloric acid. The resulting aqueous solution was purified by following the procedure described in step A of Example 5 to obtain 690 mg (78% yield) of NK631 dihydrochloride (copper-containing form) in the form of blue amorphous powder having an antimicrobial potency of 8,010 u/mg.

EXAMPLE 9

Synthesis of NK631 dihydrochloride (copper-containing form) and copper-free dihydrochloride In 10 ml of methanol, was dissolved 1.0 g of bleomycinic acid 3-aminopropyl ester dihydrochloride (copper-containing form). To the vigorously stirred solution, was added dropwise 104 mg of benzoyl chloride over a period of 30 minutes while maintaining pH of the solution at 6.5 to 7.5 by the addition of 1,4-diazabicyclo[2,2,2]octane. After stirring for additional 30 minutes, the reaction mixture was concentrated to 2 ml. To the concentrated material cooled at 0° C., was added with stirring 1.1 g of the amino compound and the mixture was stirred for 72 hours at 0° C. To the reaction mixture, was added with stirring 6 ml of cold acetone to precipitate the bleomycin components. The precipitate was collected by filtration, washed with acetone, then dissolved in 30 ml of distilled water, and immediately adjusted to pH 6.0 with 0.1 N hydrochloric acid. The resulting aqueous solution was poured into a column containing 100 ml of CM-Sephadex ® ($NH_4^+$ type) packed in 0.05 M aqueous ammonium chloride solution to allow the bleomycin components to be adsorbed. The adsorbed material was treated in a manner similar to that of step A in Example 5 to obtain 779 mg (73% yield) of NK631 dihydrochloride (copper-containing form) in the form of blue amorphous powder having an antimicrobial potency of 8,000 u/mg.

In addition, 240 mg of the unreacted bleomycic acid 3-N-benzoylaminopropyl ester monohydrochloride (copper-containing form) were recovered.

Step B: In 20 ml of distilled water, was dissolved 700 mg of the NK631 dihydrochloride (copper-containing form) obtained in step A above. The solution was poured into a column containing 65 ml of Diaion® HP-40 packed in distilled water to allow the bleomycin components to be adsorbed. The column was then washed with 200 ml of an aqueous solution containing 5% of EDTA.Na$_2$, then with 250 ml of a 5% aqueous sodium chloride solution, and finally with 100 ml of distilled water. The column was then eluted with a mixture of methanol and 0.0025 N aqueous hydrochloric acid (1:1 V/V) and 98 ml of the fraction showing ultravilet absorption at 290 mμ were collected. After removal of the methanol by distillation under reduced pressure, the residual liquid was adjusted to pH 6.0 with Dowex® 44 (OH$^-$ type) and freeze-dried to obtain 658 mg (98% yield) of NK631 dihydrochloride (copper-free form) in the form of pale yellowish white amorphous powder having an antimicrobial potency of 7,834 u/mg.

EXAMPLE 10

Synthesis of NK631 monosulfate (copper-containing form) and diacetic acid salt (copper-free form)

Step A: In 10 ml of methanol, was dissolved 1.0 g of bleomycinic acid 3-aminopropyl ester dihydrochloride (copper-containing form). To the vigorously stirred solution at room temperature, was added dropwise 104 mg of benzoyl chloride over a period of 30 minutes while maintaining pH of the solution at 5.0 to 7.5 by the addition of N-methylmorpholine. After stirring for additional 30 minutes, to the reaction mixture was added 50 ml of acetone to precipitate the bleomycin components. The precipitate was collected by filtration, washed with acetone and again dissolved in 3 ml of methanol. To the methanol solution, while being cooled at 0° C. and stirred, was added 597 mg of the amino compound and the mixture was stirred for 42 hours at 0° C. To the reaction mixture, was added with stirring 10 ml of cold acetone to precipitate the reaction product. The precipitate was collected by filtration, washed with acetone, then dissolved in 30 ml of distilled water and immediately adjusted to pH 6.0 with 0.1 N hydrochloric acid. The aqueous solution was treated with CM-Sephadex® in a manner similar to that in step A of Example 5. The fraction containing the reaction products was poured into a column containing 65 ml of Diaion® HP-40 packed in distilled water to allow the bleomycin components to be adsorbed on the resin. After washing with water, the adsorbed phase was eluted with a mixture of methanol and 0.01 N aqueous sulfuric acid (1:1 V/V) and 130 ml of a fraction showing ultraviolet absorption at 292 mμ were collected. After removal of methanol by distillation, the residual liquid was adjusted to pH 6.0 with Dowex® 44 (OH$^-$ type) and freeze-dried to obtain 813 mg (75% yield) of NK631 monosulfate (copper-containing form) in the form of blue amorphous powder having an antimicrobial potency of 7,819 u/mg.

Step B: Copper-removing treatment of 800 mg of the NK631 monosulfate (copper-containing form) obtained in step A above was carried out in the same manner as in step B of Example 9, except that in the elution stage a 5% aqueous ammonium acetate solution and a mixture of methanol and 0.01 N aqueous acetic acid (1:1 V/V) were used in place of the 5% aqueous sodium chloride solution and the mixture of methanol and 0.0025 N aqueous hydrochloric acid (1:1 V/V), respectively. There were thus obtained 748 mg (96% yield) of NK631 diacetic acid salt (copper-free form) in the form of pale yellowish white amorphous powder. The UV absorption maximum and the antimicrobial potency of this product were as shown below.

UV absorption maximum:

mμ: ($E_1^{1\%}{}_{cm}$ 0.1 HCl)

290: (105)

Antimicrobial potency: 7,620 u/mg

EXAMPLE 11

Synthesis of NK631 dihydrochloride (copper-containing form) and copper-free dihydrochloride In 3 ml of methanol, was dissolved 1.0 g of bleomycinic acid 3-aminopropyl ester dihydrochloride. To the solution, was added dropwise at room temperature 193 mg of S-tert-butoxycarbonyl-4,6-dimethyl-2-mercaptopyrimidine over a period of 60 minutes, while maintaining pH at 6.0 to 7.4 by the addition of a 14% triethylamine in methanol. The mixture was stirred for further 2 hours to yield 3N-tert-butoxycarbonylaminopropyl ester of bleomycinic acid. The mixture was then cooled to 0° C., admixed with 1.2 g of the amino compound and stirred for 70 hours. To the reaction mixture was added 10 ml of cold acetone to precipitate the bleomycin components. The precipitate was collected by filtration, washed with acetone, then dissolved in 30 ml of distilled water, and immediately adjusted to pH 6.0 with 0.1 N hydrochloric acid. The resulting aqueous solution was purified by following the procedure used in step A of Example 5 to obtain 597 mg (56% yield) of NK631 dihydrochloride (copper-containing form) in the form of blue amorphous powder having an antimicrobial potency of 8,010 u/mg.

Step B: In 50 ml of methanol, was dissolved 500 mg of NK631 dihydrochloride (copper-containing form) obtained in step A above. Into the vigorously stirred solution, was introduced hydrogen sulfide through a nozzle, 1 mm in internal diameter and dipped into the solution, for 1 hour to dissolve a large excess of hydrogen sulfide in the solution. After termination of the introduction of hydrogen sulfide, the solution was left standing for 30 minutes at room temperature. The precipitated copper sulfide was collected by filtration and washed with 50 ml of methanol saturated with hydrogen sulfide. The filtrate and washings were combined and freed from the methanol and hydrogen sulfide by distillation under reduced pressure. The residue was dissolved in 50 ml of methanol and mixed with 100 ml of ethyl ether. The precipitate formed was collected by filtration, washed with ether and dried to obtain 394 mg (82% yield) of NK631 dihydrochloride (copper-free form) in the form of pale yellowish white amorphous powder having an antimicrobial potency of 7,820 u/mg.

EXAMPLE 12

Synthesis of NK631 dihydrochloride (copper-containing form) and copper-free dihydrochloride Step A: In 2 ml of methanol, was dissolved 1.0 g of bleomycinic acid 3-aminopropyl ester dihydrochloride (copper-containing form). To the vigorously stirred solution at room temperature, was added 98 mg of salicyaldehyde while maintaining pH of the solution at 7.0 to 7.4 by the addition of triethylamine to yield bleomycinic acid 3-N-salicylideneiminopropyl ester. After 1 hour of continued stirring, to the mixture cooled to 0° C., was added with stirring 600 mg of the amino compound. The mixture was stirred for 30 hours. To the reaction mixture was added 10 ml of cold acetone to precipitate the bleomycin components. The precipitate was collected by filtration, washed with acetone, then dissolved in 30 ml of distilled water, and immediately adjusted to pH 6.0 with 0.1 N hydrochloric acid. The resulting aqueous solution was purified as in step A of Example 5 to obtain 501 mg (47% yield) of NK631 dihydrochloride (copper-containing form) having an antimicrobial potency of 8,013 u/mg.

Step B: In 25 ml of 0.5 N aqueous hydrochloric acid, was dissolved 450 mg of the NK631 dihydrochloride (copper-containing form) obtained in step A above. To the solution was added 25 ml of a chloroform solution containing 0.2% of dithizon (diphenylthiocarbazone). After rapid shaking and mixing, the mixture was allowed to stand still, whereby the mixture separated into two layers. The lower layer (chloroform layer) was drawn off and the upper layer was mixed with 25 ml of the fresh chloroform solution containing dithizon. The above procedure of shaking, phase separation, and addition of fresh chloroform solution containing dithizon was repeated eight times. Finally the upper layer (aqueous layer) was washed with chloroform and the separated aqueous layer was adjusted to pH 6.0 with Dowex® 44 (OH⁻ type). The aqueous layer thus treated was evaporated under reduced pressure to dryness to obtain 415 mg (96% yield) of NK631 dihydrochloride (copper-free form) in the form of pale yellowish white amorphous powder having an antimicrobial potency of 7,845 u/mg.

EXAMPLE 13

Synthesis of NK631 dihydrochloride (copper-containing form)

In 2 ml of methanol, was dissolved 1.0 g of bleomycinic acid 3-aminopropyl ester dihydrochloride (copper-containing form). To the solution cooled to 0° C., was added with stirring 1.0 g of the amino compound and the mixture was stirred for further 72 hours. To the reaction mixture, was added with stirring 6 ml of cold acetone to precipitate the bleomycin components. The precipitate was purified as in step A of Example 5 to obtain 128 mg (12% yield) of NK631 dihydrochloride (copper-containing form) in the form of blue amorphous powder having an antimicrobial potency of 8,015 u/mg.

REFERENCE EXAMPLE 1

Synthesis of N-[(S)-1'-phenylethyl]-1,3-diaminopropane

To 50 g of (S)-1-phenylethylamine at 0° C. with cooling, was added with stirring 33 g of acrylonitrile. The mixture was placed in a flask provided with a reflux condenser connected to a calcium chloride tube and was heated to 93° C. at which temperature the mixture was stirred for 18 hours. After completion of the reaction, the reaction mixture was freed from the excess acrylonitrile by distillation under reduced pressure. The residue was distilled under reduced pressure and a fraction boiling at 142° to 145° C./7 mmHg was collected to obtain 53.5 g of 3-[(S)-1'-phenylethylamino]propionitrile. This nitrile was placed in an autoclave together with 5 g of Raney nickel W-7 and 50 ml of ethanol containing 15% of ammonia. The mixture was stirred at a speed of 1,000 rpm for 1.5 hours, at 50° to 58° C., and under a hydrogen partial pressure of 100 to 40 kg/cm². After completion of the reduction, the reaction mixture was distilled under reduced pressure. A fraction boiling at 95°–103° C./2 mmHg was collected to obtain 48.3 g of N-[(S)-1'-phenylethyl]-1,3-diaminopropane [66% theoretical yield from (S)-1-phenylethylamine].

What is claimed is:

1. A method for producing 3-[(S)-1'-phenylethylamino] propylaminobleomycin represented by the formula

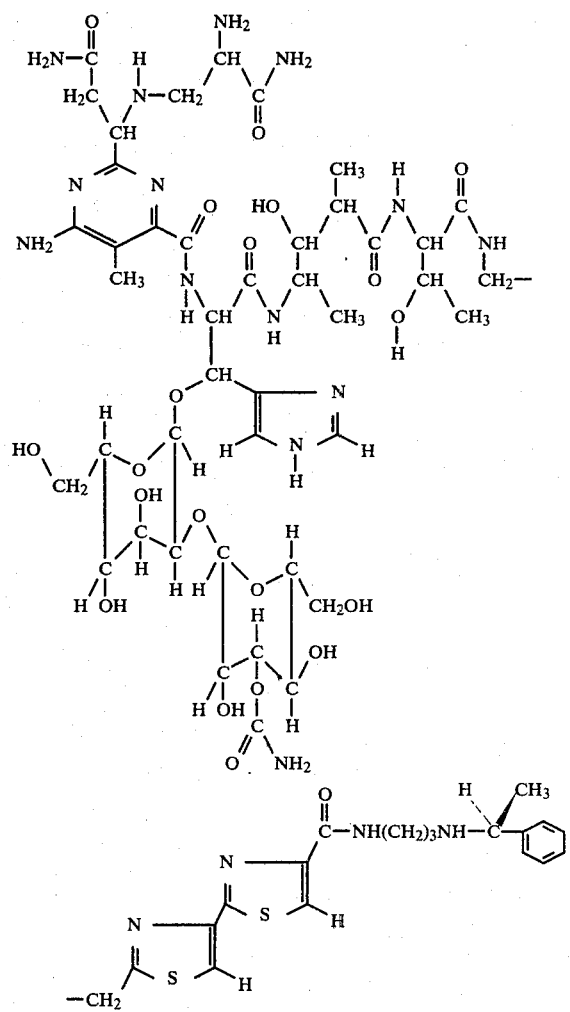

and a non-toxic salt thereof, which comprises reacting a reactive derivative of the carboxylic group of the bleomycinic acid represented by the formula

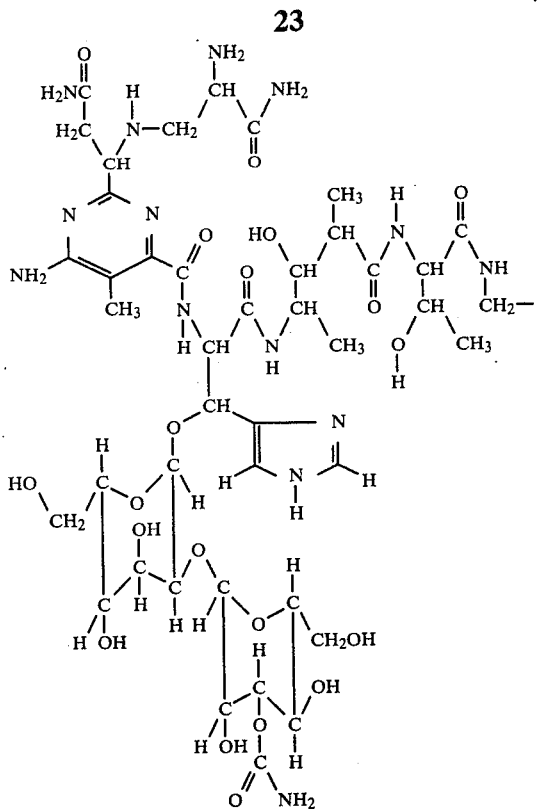

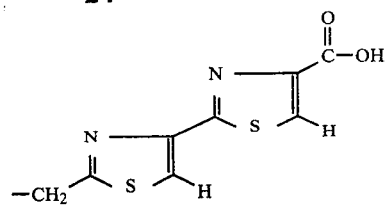

2. A method according to claim 1, wherein the non-toxic salt is hydrochloride, sulfate or acetic acid salt.

3. A method according to claim 1, wherein 1 to 10 equivalents of the N-[(S)-1'-phenylethyl]-1,3-diaminopropane are used for one equivalent of the bleomycinic acid.

4. A method according to claim 1, wherein the bleomycinic acid and the N-[(S)-1'-phenylethyl]-1,3-diaminopropane are allowed to react at 0° to 30° C. for 1 to 24 hours.

5. A method according to claim 1, wherein the solvent is dimethylformamide, diethylsulfoxide or a mixture thereof.

* * * * *

UNITED STATES PATENT AND TRADEMARK OFFICE
CERTIFICATE OF CORRECTION

PATENT NO. : 4,238,391
DATED : December 9, 1980
INVENTOR(S) : Tomohisa Takita et al It is certified that error appears in the above—identified patent and that said Letters Patent is hereby corrected as shown below:

Column 24, after last formula in Claim 1, the following was omitted during the printing process:

— , wherein the reactive derivative of the carboxylic group of the bleomycinic acid is prepared by using 6-chloro-1-p-chlorobenzenzsulfonyloxybenzotriazole, with N-[(S)-1'-phenylethyl]-1, 3-diaminopropane in a solvent selected from the group consisting of dimethylformamide, diethylsulfoxide, methanol and a mixture thereof and, if necessary, converting the product into a non-toxic salt —

Signed and Sealed this

Twelfth Day of May 1981

[SEAL]

Attest:

RENE D. TEGTMEYER

*Attesting Officer*   *Acting Commissioner of Patents and Trademarks*